(12) United States Patent
Schwaibold

(10) Patent No.: US 11,921,011 B2
(45) Date of Patent: Mar. 5, 2024

(54) MONITORING SYSTEM FOR DETECTING LEAKAGES DURING VENTILATION, AND METHOD

(71) Applicant: Loewenstein Medical Technology S.A., Luxembourg (LU)

(72) Inventor: Matthias Schwaibold, Karlsruhe (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 220 days.

(21) Appl. No.: 17/174,654

(22) Filed: Feb. 12, 2021

(65) Prior Publication Data

US 2021/0255055 A1 Aug. 19, 2021

(30) Foreign Application Priority Data

Feb. 14, 2020 (DE) .......................... 102020104008.3

(51) Int. Cl.
*G01M 3/28* (2006.01)
*A61M 16/00* (2006.01)

(52) U.S. Cl.
CPC .......... *G01M 3/28* (2013.01); *A61M 16/0003* (2014.02); *A61M 2205/15* (2013.01)

(58) Field of Classification Search
CPC ................ G01M 3/28; A61M 16/0003; A61M 2205/15; A61M 16/1045; A61M 16/0069; A61M 16/06; A61M 2205/18; A61M 16/0666; A61M 16/1075; A61M 2016/0021; A61M 2016/0027; A61M 2202/0208; A61M 2205/3334; A61M 2205/3584; A61M 2205/3341; A61M 16/0051; A61M 2016/0039;
(Continued)

(56) References Cited

U.S. PATENT DOCUMENTS 11,420,002 B2 * 8/2022 Evans .................... A61M 16/14
11,471,627 B2 * 10/2022 Evans ................ A61M 16/0003
(Continued)

FOREIGN PATENT DOCUMENTS

CA 2361631 C * 5/2008 .......... A61M 16/024
DE 102007039004 A1 3/2008
(Continued)

OTHER PUBLICATIONS

T. J. Meyer and et al, "Air Leaking Through the Mouth During Nocturnal Nasal Ventilation: Effect on Sleep Quality", 1997 American Sleep Disorders Association and Sleep Research Society, Sleep, 20(7):561-569 (Year: 1997).*
(Continued)

*Primary Examiner* — Douglas Kay
(74) *Attorney, Agent, or Firm* — Abel Schillinger, LLP

(57) ABSTRACT

A monitoring system for detecting leakages during ventilation with a ventilator, comprising a monitoring device for determining a leakage rate from a leakage parameter detected by sensors. The monitoring device is configured for recording a time profile of the leakage parameter, for determining a measure for a rate of change of the leakage parameter in the time profile, and for detecting a mouth leakage in accordance with the measure, such that a mouth leakage can be differentiated from at least one other leakage type.

19 Claims, 4 Drawing Sheets

(58) Field of Classification Search
CPC .... A61M 2205/3553; A61M 2205/505; A61M 2205/583; A61M 2205/8212; A61M 2230/202; A61M 2230/205; A61M 2230/46; A61M 16/101; A61M 16/024; A61B 5/4836; A61B 5/14551; A61B 5/11; A61B 5/4542; A61B 5/4809

See application file for complete search history.

(56) References Cited

U.S. PATENT DOCUMENTS

| | | | |
|---|---|---|---|
| 2010/0186741 A1* | 7/2010 | Aylsworth | A61M 16/12 128/203.29 |
| 2013/0317765 A1* | 11/2013 | Rao | A61M 16/00 702/51 |
| 2014/0007878 A1 | 1/2014 | Armistead et al. | |
| 2018/0126104 A1* | 5/2018 | Krüger | A61M 16/0003 |
| 2019/0172371 A1* | 6/2019 | Eckert | G09B 23/303 |
| 2019/0344026 A1* | 11/2019 | Rao | A61M 16/00 |
| 2021/0113795 A1* | 4/2021 | Austin | A61M 16/024 |
| 2022/0088328 A1* | 3/2022 | Rao | G01M 3/04 |

FOREIGN PATENT DOCUMENTS

| | | | |
|---|---|---|---|
| JP | H11344364 A | * 12/1999 | |
| WO | WO-0191841 A1 | * 12/2001 | ........ A61M 16/0051 |
| WO | 2012012835 A2 | 2/2012 | |
| WO | 2012126041 A1 | 9/2012 | |

OTHER PUBLICATIONS

S. Mehta and et al, "Leak compensation in positive pressure ventilators: a lung model study", European Respiratory Journal 2001; 17: 259-267 (Year: 2001).*

M. A. Balzan and et al, "Leak Profile Inspection During Nasal Continuous Positive Airway Pressure", Respiratory Care • May 2011 vol. 56 No. 5 (Year: 2011).*

Lebret, Marius, Nathalie Arnol, Jean-Benoît Martinot, Loïc Lambert, Renaud Tamisier, Jean-Louis Pepin, and Jean-Christian Borel. "Determinants of unintentional leaks during CPAP treatment in OSA." Chest 153, No. 4 (2018): 834-842 (Year: 2018).*

* cited by examiner

MONITORING SYSTEM FOR DETECTING LEAKAGES DURING VENTILATION, AND METHOD

CROSS-REFERENCE TO RELATED APPLICATIONS

The present application claims priority under 35 U.S.C. § 119 of German Patent Application No. 102020104008.3, filed Feb. 14, 2020, the entire disclosure of which is expressly incorporated by reference herein.

BACKGROUND OF THE INVENTION

1. Field of the Invention

The present invention relates to a monitoring system for detecting leakages during ventilation, and to a method for operating such a system. The monitoring system comprises at least one monitoring device for determining a leakage rate from at least one leakage parameter detected by one or more sensors.

2. Discussion of Background Information

Leakages are a central problem in non-invasive ventilation. There are essentially two types of leakages, and they have different effects and can be remedied in different ways: mask leakages and mouth leakages. Mask leakage can in most cases be remedied by correcting the mask or the fit of the mask. Mouth leakage can generally be remedied by closing the mouth. Moreover, there are also what are called desired leakages, which serve for example to flush the exhaled air out of the mask.

The detection of a leakage, and of its strength or leakage rate, is very important for the success of ventilation. It is also important to detect the type of leakage and in particular to differentiate between the two types of leakage mentioned above. Knowledge of the leakage type is most essential for an optimal correction of the leakage and for the appropriate care of the patient. This is generally only possible by hospital admission and additional sensors or visual observation of the patient.

The leakages generally also have a decisive effect on the energy consumption and often also on the noise emissions of the appliance. To compensate for the leakage losses, an increased fan speed is necessary in most cases. This leads to higher power consumption. Particularly in the case of mobile appliances, this is a great disadvantage since the battery time can drop considerably. Moreover, increased fan noise occurs in most cases. This is found to be inconvenient, for example in the context of sleep therapy.

In view of the foregoing, it would be advantageous to be able to improve the handling of such leakages during ventilation. In particular, it would be advantageous to have available a simple and at the same time particularly reliable detection of the leakage type. Preferably, even inexperienced users or patients should be able to reliably detect and remedy leakages. Preferably, it should be possible to use the improvement advantageously in the field of telemedicine and/or in home ventilation.

SUMMARY OF THE INVENTION

The present invention provides a monitoring system and a method as set forth in the independent claims. Developments and advantageous configurations are the subject matter of the dependent claims. Further advantages and features will become apparent from the general description and from the description of the illustrative embodiments.

The monitoring system according to the invention serves for detecting leakages during ventilation with at least one ventilator. The monitoring system comprises at least one monitoring device for in particular automatic determination of a leakage rate from at least one leakage parameter detected by one or more sensors. The monitoring device is suitable and configured for recording at least one time profile of the at least one leakage parameter, and for determining at least one measure for a rate of change of the leakage parameter in the time profile. The monitoring device is suitable and configured for detecting at least one mouth leakage in accordance with the measure, or for identifying it as such, and preferably for thereby differentiating it from at least one other leakage type.

The monitoring system according to the invention affords many potential advantages. A considerable advantage is afforded by the automatic detection of the leakage type. A mouth leakage is reliably and easily detected in this way. Thus, even inexperienced users can establish that a mouth leakage is present and can remedy this situation by suitable measures. Hospital stays and time-consuming and cost-intensive observation of the patient can thus be avoided or at least reduced. The invention also allows leakages and their causes to be established reliably and conveniently in the context of home ventilation or telemedicine.

Moreover, the energy consumption is also considerably reduced by virtue of the automatic detection and the particularly simple elimination of the leakages. The battery time can thus be prolonged, or the weight and size of the appliances can be reduced by using smaller batteries. Moreover, undesired noise emissions from the appliance are avoided, of the kind that otherwise occur when compensating for leakage losses.

It is preferable and advantageous that the monitoring device is suitable and configured for detecting the presence of an abrupt leakage reversal using the measure for the leakage change. In particular, the monitoring device preferably is suitable and configured for assuming a mouth leakage at least in accordance with an abrupt leakage reversal being present. The use of such abrupt leakage reversals affords a particularly reliable possibility for the automatic detection of mouth leakages. The monitoring device assumes a mouth leakage in particular when an abrupt leakage reversal is present. The presence of an abrupt leakage reversal can be detected in particular from the measure for the rate of change. In particular, the measure for the rate of change then indicates a particularly strong and at the same time particularly quick reversal of the leakage. In particular, the leakage rate falls abruptly and considerably.

Preferably, an abrupt leakage reversal is present when the leakage rate falls by at least about 10% and in particular by at least about 20% and preferably by at least about 30% within a defined time period. The leakage rate can also fall by at least about 5% or about 15% or about 40% or also about 50% or about 100% or about 150% or about 200% or about 300% within the defined time period, so that in the context of the present invention an abrupt leakage reversal is present. Such reversals are particularly characteristic of the termination of leakages by closure of the mouth.

Preferably, an abrupt leakage reversal is present when the leakage rate falls by the defined measure within a maximum of about eight breaths and preferably a maximum of about six breaths and particularly preferably a maximum of about four breaths. The leakage rate can also fall by the defined measure within a maximum of about seven breaths or a maximum of about five breaths or also a maximum of about three breaths, such that an abrupt leakage reversal is present. It is also possible that the leakage rate has to fall within a maximum of about two breaths or during just one breath. Such a relationship to the breaths has proven particularly advantageous for the determination of abrupt leakage reversals.

It is possible that the monitoring device is suitable and configured for determining and outputting a characteristic number for the incidence of abrupt leakage reversals per unit of time and in particular per hour. The characteristic number can also determine and output the incidence of abrupt leakage reversals over several hours or over the entire duration of therapy. Such characteristic numbers permit a very rapid and at the same time reliable indication concerning the quality of ventilation in terms of the leakage.

In all of the embodiments, it is particularly preferable that the monitoring device is suitable and configured for detecting a mouth leakage at least in accordance with whether the at least one leakage parameter changes, in particular decreases, by at least a defined measure within at least one defined time period. It is then assumed in particular that there is an abrupt leakage reversal. Such a change of the leakage parameter can be used as a necessary condition or also as a sufficient condition for the detection of a mouth leakage. As to whether the leakage parameter has changed by the defined measure within the defined time period, the monitoring device detects this in particular from the measure for the rate of change of the leakage parameter. For example, the measure for the rate of change is a gradient and/or a derivative and/or another variable of functional analysis.

The defined time period is in particular a maximum of about 30 seconds and preferably a maximum of about 15 seconds and particularly preferably a maximum of about 10 seconds. It is also possible and advantageous that the defined time period is a maximum of about 8 seconds or a maximum of about 5 seconds or a maximum of about 3 seconds or a maximum of about 2 seconds or also a maximum of just 1 second. In particular, the defined time period is between about three and about 30 seconds. Such time periods have proven particularly reliable for the identification of mouth leakages.

The leakage parameter is in particular a flow of a gas stream relating to the ventilation. The flow can also be designated as volumetric flow. In particular, the leakage parameter is a flow. In particular, the leakage parameter describes how much volume of respiratory gas escapes per unit of time through the leakage (for example from the mouth or between mask and face). The leakage parameter can also be the pressure of a gas stream relating to the ventilation. Defined measures in particular for the change of the pressure are then stored in order to permit an assignment to defined leakage types.

A defined measure for the change of the flow is in particular at least about 10 l/min and preferably at least about 15 l/min and particularly preferably at least about 25 l/min. The defined measure can also be at least about 5 l/min or at least about 8 l/min or at least about 12 l/min or at least about 18 l/min or at least about 20 l/min. Such changes of the flow have proven particularly reliable for the detection of mouth leakages.

The monitoring device can be suitable and configured for detecting the leakage type on the basis of whether the flow or a statistical value of the flow, for example an average, lies above a limit value. It could be observed that, under certain conditions, the flow is higher in the case of a mouth leakage than it is, for example, in the case of mask leakages.

In an advantageous embodiment, the monitoring device is suitable and configured for not taking account and/or for taking only weighted account of a time period in the time profile of the leakage parameter for the detection of the leakage type when the leakage rate, after the abrupt leakage reversal (i.e., after the change of the leakage parameter by the defined measure within a defined time period), still lies above a limit value and in particular above about 25 l/min. The limit value can also be provided to be about 30 l/min or about 35 l/min or about 40 l/min or more. The limit value can also be about 20 l/min or about 15 l/min. This permits particularly reproducible detection of the leakage type.

The monitoring device is preferably suitable and configured for not outputting the detection of the leakage type and/or for outputting it with at least one warning when the leakage rate (e.g., on average and/or over a defined time period) is about 50 l/min or more. A value of at least about 30 l/min or at least about 40 l/min or at least about 60 l/min can also be provided for this purpose. It is possible that at least one alarm is output in the case of such a high leakage rate. It is also possible that the monitoring device rejects, or gives only weighted account to, the leakage parameters that are detected during a time with such high leakage rates.

In a particularly advantageous development, the monitoring device is suitable and configured for detecting the leakage type, and in particular for detecting mouth leakage, by also at least taking account of how often abrupt leakage reversals occur and/or how regularly abrupt leakage reversals occur. Incidence and regularity are particularly characteristic features of mouth leakages. In particular, the monitoring device considers the reaching of a minimum limit for the incidence and/or regularity as at least one necessary condition for the presence of a mouth leakage. If such a minimum limit is not reached, this is taken in particular as a necessary condition for the presence of a mask leakage.

In an advantageous embodiment, the monitoring device is suitable and configured for determining the time difference between one abrupt leakage reversal and a past abrupt leakage reversal. Preferably, for detecting the mouth leakage, the monitoring device at least also takes account of how great the difference is between successive abrupt leakage reversals. In particular, a time difference below a limit value is used as a necessary condition for the detection of a mouth leakage. For example, in the case of a mouth leakage, abrupt leakage reversals lie only a few minutes or a few seconds and/or a few breaths apart.

The monitoring device is preferably suitable and configured for detecting the mouth leakage by also taking account of arousal events on the part of the patient, and in particular by taking account of a time overlap of an arousal event with the start of an abrupt leakage reversal as at least one necessary condition for the presence of a mouth leakage. The arousal event can be detected by sensors of the monitoring system and/or via an appliance coupled thereto. It has been found that arousal events are particularly often associated with closing of the open mouth and thus also often cause abrupt leakage reversals.

It is possible and preferable that the monitoring device is suitable and configured for determining a desired leakage rate and/or a leakage rate of another kind by using the leakage rate that still remains after closure of a detected mouth leakage. In particular, the leakage rate that still remains at the end and/or at the minimum of the abrupt leakage reversal is taken into account for this purpose. For determination of the desired leakage rate, an irrigation flow in particular is also taken into account.

It is also possible and preferable that the monitoring device is suitable and configured for deriving a strength of the mouth leakage, in particular the proportion of the mouth leakage in the leakage rate, via a degree of the reversal of the leakage rate by closure of the mouth. For example, the degree of the reversal can be determined as the difference in the leakage rate before and after termination of the mouth leakage.

The monitoring device can also be suitable and configured for using a detected mouth leakage as at least one necessary and/or sufficient condition for the detection of an arousal event on the part of the patient. Such an embodiment is particularly advantageous if the sleep behavior of the patient is also monitored with the monitoring system. It has been found that closure of the mouth generally takes place upon waking up or arousal.

In all of the embodiments, it is particularly preferable that the monitoring device is suitable and configured for detecting a mask leakage as at least one other leakage type, and preferably for differentiating a mouth leakage and a mask leakage from each other.

The monitoring device is preferably suitable and configured for differentiating the mask leakage from the mouth leakage at least by a duration for which a defined leakage rate is maintained. The monitoring device can also differentiate the mask leakage from the mouth leakage at least by a number of defined reversals of the leakage, and in particular by a number of abrupt leakage reversals. This offers a particularly reliable differentiation between mouth leakages and mask leakages, since mask leakages are often maintained almost unchanged over a long period of time, for example over several hours or during the entire night sleep.

The present invention also provides a monitoring system as set forth above in which the monitoring device is suitable and configured for recording at least one time profile of the leakage parameter and for determining at least one measure for a rate of change of the leakage parameter in the time profile and for detecting at least one mask leakage in accordance with the measure.

In particular, the monitoring device may be suitable and configured for carrying out a detection of the leakage type during ventilation at defined time intervals and/or continuously, and in particular for recording detected leakage types and preferably outputting them via at least one display device. In particular, the detected leakage type may be output with at least one other parameter. For example, the number of mouth leakages and/or the leakage rate and/or a mean duration of the leakage and the like are displayed at the same time.

In all of the embodiments, it is preferable that the monitoring device is suitable and configured for executing at least one action in accordance with a detected leakage type. The action preferably comprises at least one output of at least one warning and/or at least one alarm and/or at least one action description in particular for avoiding leakages.

In an advantageous development, the monitoring device is suitable and configured for actuating the ventilator in accordance with a detected leakage type and for adapting at least one control variable of the ventilator, in particular in order to obtain a decrease in the leakage rate and/or the leakage incidence. At least one respiration parameter can also be adapted or regulated to a setpoint value.

The monitoring system can comprise at least one ventilator. The ventilator is in particular suitable and configured for being actuated by the monitoring device. The ventilator is configured in particular for ventilation in the form of CPAP and/or APAP. In particular, the ventilator is suitable and configured for generating at least one defined stream of respiratory gas for ventilation by means of at least one ventilation device.

It is possible that the monitoring system is formed separately from the ventilator. For example, the monitoring device is for this purpose accommodated in a housing separate from the ventilator and can be coupled to the latter by wires and/or wirelessly via at least one interface.

The method according to the invention serves for operating a monitoring system as described above. Such a method also achieves the aforementioned object in a particularly advantageous manner.

In particular, the method is such that the above-described actions of the monitoring device are executed. In particular, the above-described monitoring system is suitable and configured for being operated by the method according to the invention. In the context of the present invention, provision is made in particular that the monitoring device is suitable and configured for implementation of the method features or steps described herein.

Mouth leakage is caused in particular by respiratory gas escaping through a mouth that is at least partially opened during ventilation. Mouth leakage leads in particular to a pressure loss and/or volume loss. With mouth leakage, closure of the mouth generally leads to an abrupt leakage reversal. Other leakage types, for example mask leakage, generally remain unchanged after the mouth is closed.

Mask leakage is characterized in particular by a flow of respiratory gas escaping in an undesired manner from a mask or from another patient interface during ventilation. Correcting the fit of the mask generally leads to a measurable reversal of the mask leakage. However, the leakage reversal takes place significantly less abruptly than by closure of the mouth in the case of mouth leakage.

The leakage reversal that is characteristic of mouth leakage occurs particularly in a time period that is characteristic of the closure of the mouth. The leakage reversal characteristic of mask leakage occurs in particular in a time period that is characteristic of the adaptation of the mask by the patient.

It is therefore preferable that the defined time period for the change of the leakage parameter in the case of mask leakage is greater than in mouth leakage by at least a factor of two or at least a factor of three or at least a factor of four or at least a factor of five or also at least a factor of ten or at least a factor of about 20 or more.

In the context of the present invention, a leakage is at all times understood in particular as an undesired leakage. In particular, in the context of the present invention, the leakage rate already takes into account a desired leakage. For example, an irrigation flow is automatically deducted.

The leakage rate reflects in particular a strength of the leakage. The leakage rate is in particular defined by a volume loss and/or pressure loss. The leakage rate is in particular calculated from the at least one leakage parameter detected by sensors. The leakage parameter is for example a flow, also designated as volumetric flow, a pressure or pressure profile and/or a combination of such variables.

For the detection of the leakage parameter, at least one sensor element is provided in particular. The sensor element can be part of the monitoring system and/or can be provided by the ventilator. For example, the ventilator has at least one sensor device for controlling or regulating the ventilation, which sensor device can also be used to detect the leakage type. For example, a flow sensor and/or pressure sensor or the like is provided.

BRIEF DESCRIPTION OF THE DRAWINGS

Further advantages and features of the present invention will become clear from the description of illustrative embodiments, which are explained below with reference to the accompanying drawings, in which.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
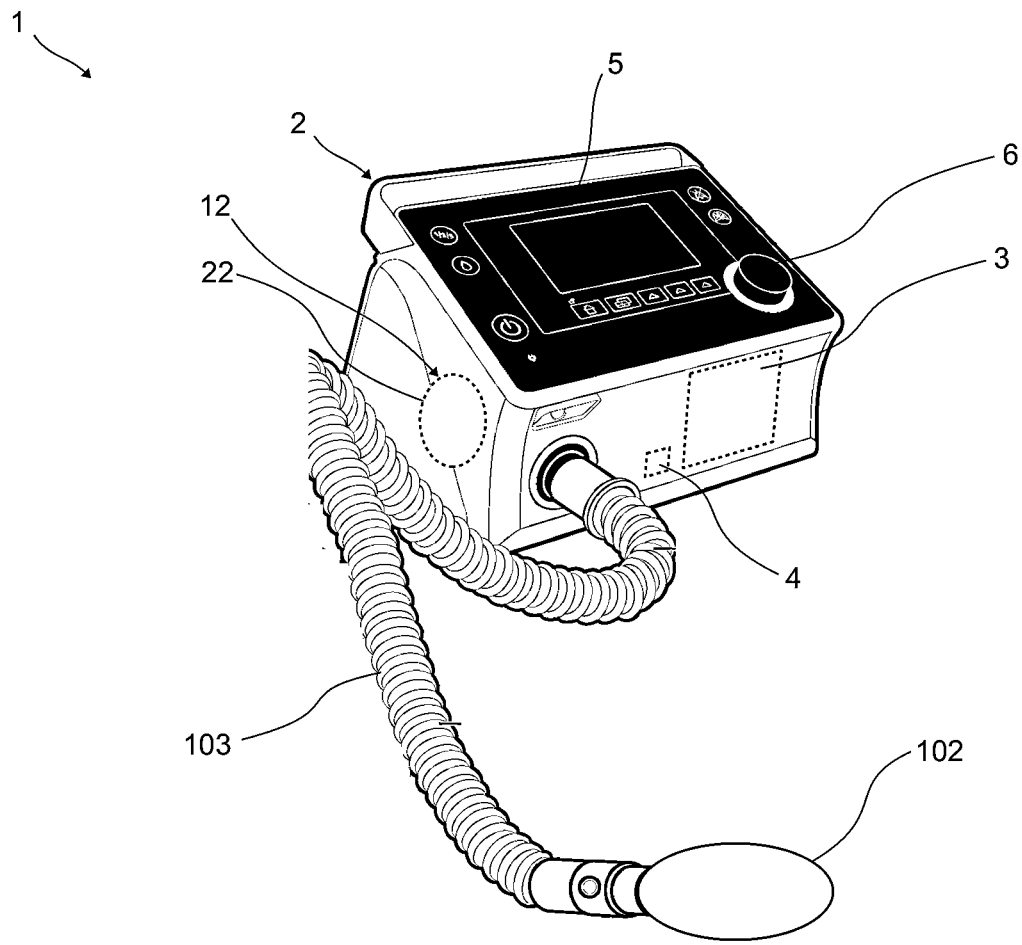
FIG. 1 shows a purely schematic and perspective view of a monitoring system according to the invention.

FIG. 1 shows a monitoring system 1 according to the invention, with a monitoring device 3 for detecting leakages during non-invasive ventilation with a ventilator 2. The ventilator 2 is here part of the monitoring system 1 and provides the housing of the monitoring device 3. The monitoring device 3 can alternatively also be arranged as a separate device outside the ventilator 2. The system 1 shown here is operated by the method according to the invention. The monitoring system 1 is configured here as a home ventilator. However, the monitoring system 1 can also be used for ventilation in a hospital environment.

In the interior of its housing, the ventilator 2 here has a ventilation device 12 which is equipped with a fan 22 for generating a respiratory gas flow. The respiratory gas flow is supplied to the patient via a tubing 103 which is coupled to the ventilation device 12 and which has a breathing mask 102. Alternatively to the breathing mask 102, other patient interfaces can also be used. In addition to or as an alternative to the fan 22, a compressed gas source can also be provided.

The ventilator 2 here comprises a display device 5 and an operating device 6. Combinations of operating device 6 and display device 5 can also be provided, for example in the form of a touch-sensitive display surface or a touch screen. Here, the display device 5 also serves to show information from the monitoring device 3 and for example the leakage type and the leakage rate. However, the monitoring device 3 can also output its information on further display devices not shown here, e.g. on a computer display or a tablet or smartphone or the like.

The ventilation device 12 is here operatively connected to a sensor element 4 which has one or more sensors for detecting respiration parameters and leakage parameters and, if appropriate, further variables characteristic of the respiration. For example, the sensor element 4 comprises a pressure sensor (not shown in detail here) which detects the pressure conditions of the respiratory gas flow, and/or a flow sensor which detects the flow.

The sensor element 4 is also operatively connected here to the monitoring device 3, such that the detected variables can also be at least partially processed by the monitoring device 3. The monitoring device 3 can also comprise its own sensor element 4. For example, the monitoring device 3 determines the leakage rate from at least one parameter detected by sensors and, for example, a flow.

The ventilation device 12 here comprises a control device which is arranged in a concealed fashion inside the housing and which actuates the fan 22. For example, CPAP ventilation or APAP ventilation can be carried out. The ventilation device 12 is switched, for example, to a defined respiratory gas flow and/or a respiratory gas pressure for ventilation. The control device 12 can make available a required minimum pressure and/or can compensate for pressure fluctuations that are caused by the breathing activity of the user. For example, the control device 12 detects, by way of the sensor means 4, the current pressure in the breathing mask 102 and regulates the power of the fan 22 accordingly, until a desired respiratory pressure is present.

Moreover, the ventilation device 12 can also be actuated here by the monitoring device 3. For this purpose, the monitoring device 3 is operatively connected to the control device.

Ventilator parameters that can be controlled via the detection of the leakage types include the ones described below for example.

If a very considerable mask leakage is detected, at least one therapy pressure level can be lowered in order to reduce the mask leakage.

If a mouth leakage is detected, it is possible, preferably in combination with an evaluation of the inspiratory respiratory flow profile, to increase at least one therapy pressure level in order to treat partial airway obstructions that have led to increased respiratory effort with mouth opening.

If a mouth leakage is detected, the power level for humidifying and warming the respiratory air can be increased in order to prevent the mucous membranes from drying out.

The precision of the differentiation between mask leakage and mouth leakage can be improved by way of additional sensors connected to the appliance. In particular by automatic evaluation of: measurement of the mouth opening, e.g. via strain gauges in a chin strap or via distance sensors placed above and below the mouth; image recognition from a photo, video recording or IR scan of the patient; flow sensor, e.g. thermistor, which is placed in the region of the eventual respiratory flow in front of the mouth.

The relevance of a mouth leakage or mask leakage can be determined by way of additional sensors connected to the appliance, e.g. with a $SpO_2$ sensor (pulse oximeter) or $CO_2$ sensor (e.g. $ptCO_2$) and evaluation of the blood gases in phases with and without leakages.

To detect leakages during ventilation and to be able to differentiate between different types of leakages, at least one time profile of one or more leakage parameters is recorded here. From the time profile, at least one measure is then determined for a rate of change of the leakage parameter over time. Depending on the measure, the mouth leakage can then be differentiated from another leakage type and, for example, from a mask leakage.

Mouth leakages are distinguished by being repeatedly interrupted by sudden mouth closure, e.g. upon swallowing, during arousal events, or cyclically in the case of sleep-related respiratory disturbances. By contrast, mask leakages end less abruptly, typically by better manual fixing of the mask or of the straps.

An advantage of the invention is that abrupt leakage reversals or leakage termination processes can be detected, their incidence can be counted, and they can be used as an indicator of the presence of mouth leakages. In one illustrative embodiment, after an abrupt fall in the leakage (state with the mouth just closed), the leakage level is estimated and identified as the strength of the mask leakage.

In addition, the strength of the mouth leakage can be estimated on the basis of the degree of the reversal. If the strengths of the mouth leakage and mask leakage can thus be estimated at several sample points in the course of the therapy, the overall leakage during the therapy (for example either the average or median or weighted average or percentile) can also be divided up into an estimate of the mouth leakage and mask leakage as a share of the overall strength.

One illustrative embodiment provides the following: evaluation of the leakage signal and search for a depression of the signal by at least x l/min in at most y seconds, with x in the preferred range of about 10 to about 40 and y in the range of about 3 to about 30.

For example, via an output on the appliance or in accompanying software or telemonitoring, it is then not only the strength of the leakage that can be output as before, but also an indicator of the type of leakage, e.g. mask leakage or mouth leakage, or both in parallel.

Figure 2:
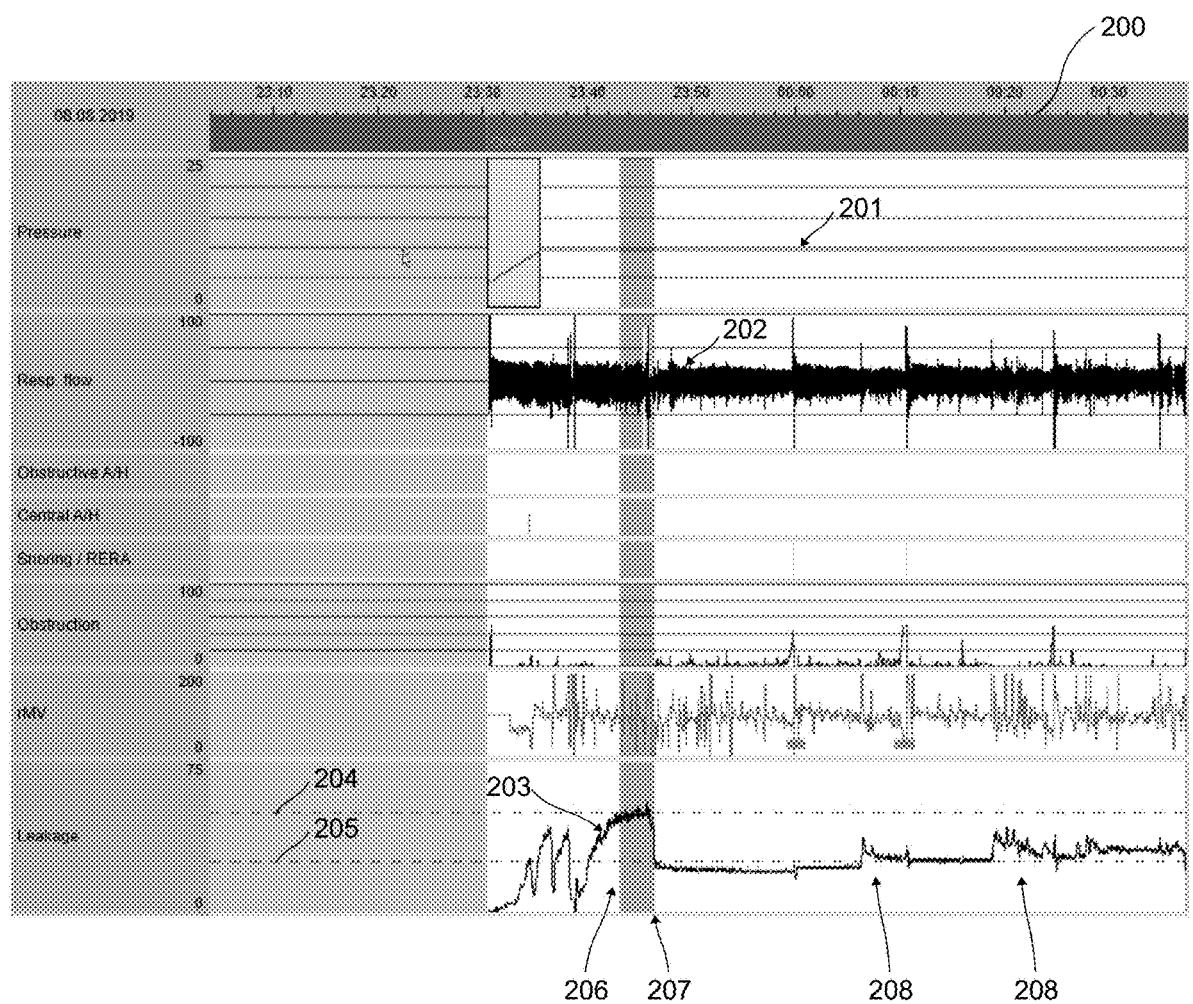
FIG. 2 shows a highly schematic graph with profiles of leakage parameters in order to explain the detection of leakages by means of the invention.

FIG. 2 shows an example of a respiration profile with leakage types detected according to the invention. To this end, a leakage rate 203 was plotted here, and its leakage change over time was evaluated. The leakage rate 203 corresponds here to a flow in l/min. The leakage rate 203 and further respiration parameters are detected by corresponding sensor means 4 during ventilation and are recorded as profiles over the time 200. The respiration parameters are here, for example, the respiratory gas pressure 201 and the respiratory gas flow 202, and also further parameters helpful for the ventilation.

The monitoring device 3 is configured such that it can detect the mouth leakage 206 and the mask leakages 208 from the leakage rate 203 shown here.

The rate of change of the leakage rate 203 changes here over the time 200. A particularly abrupt leakage reversal 207 is marked here by the reference sign 207. At this time, the leakage rate 203 falls by more than 25 l/min within only a few seconds. It can therefore be assumed with a high degree of probability that the leakage reversal 207 was caused by the closure of the mouth. The leakage rate 203 observed beforehand can thus be attributed, likewise with a high degree of probability, to a mouth leakage 206.

By closure of the mouth, the leakage rate 203 falls here by more than 15 l/min within a maximum of 10 seconds, which for example is stored in the monitoring device 3 as a condition for the detection of mouth leakage 206. Moreover, for detection of a mouth leakage, provision is made that that the leakage rate 203 after closure of the mouth has to fall to a maximum of 25 l/min so that a reliable evaluation can be ensured. If the leakage rate after the leakage reversal 207 still lies above 25 l/min, the monitoring device 3 rejects this event.

For the detection of the mouth leakage, limits values 204, 205 are taken into consideration here. If the limit value 204 is exceeded, this indicates an opened mouth. If the limit value 205 is undershot, this indicates a closed mouth.

The leakage rate 203 detected after the leakage reversal 207 can moreover be assumed as a desired leakage rate 203 or a customary background rate.

Thereafter, the leakage rate 203 increases again here and becomes more irregular. However, the reversals of the leakage rate 203 are not abrupt here, as in the case of closure of the mouth, and instead they proceed very slowly and rise again. It can be assumed that mask leakages 208 are involved here. It can be clearly seen here that the mask leakage 208 does not end abruptly and basically does not end at all. Generally, the mask leakage 208 ends only when the patient is awake and the mask 102 is repositioned and fixed.

Figure 3:
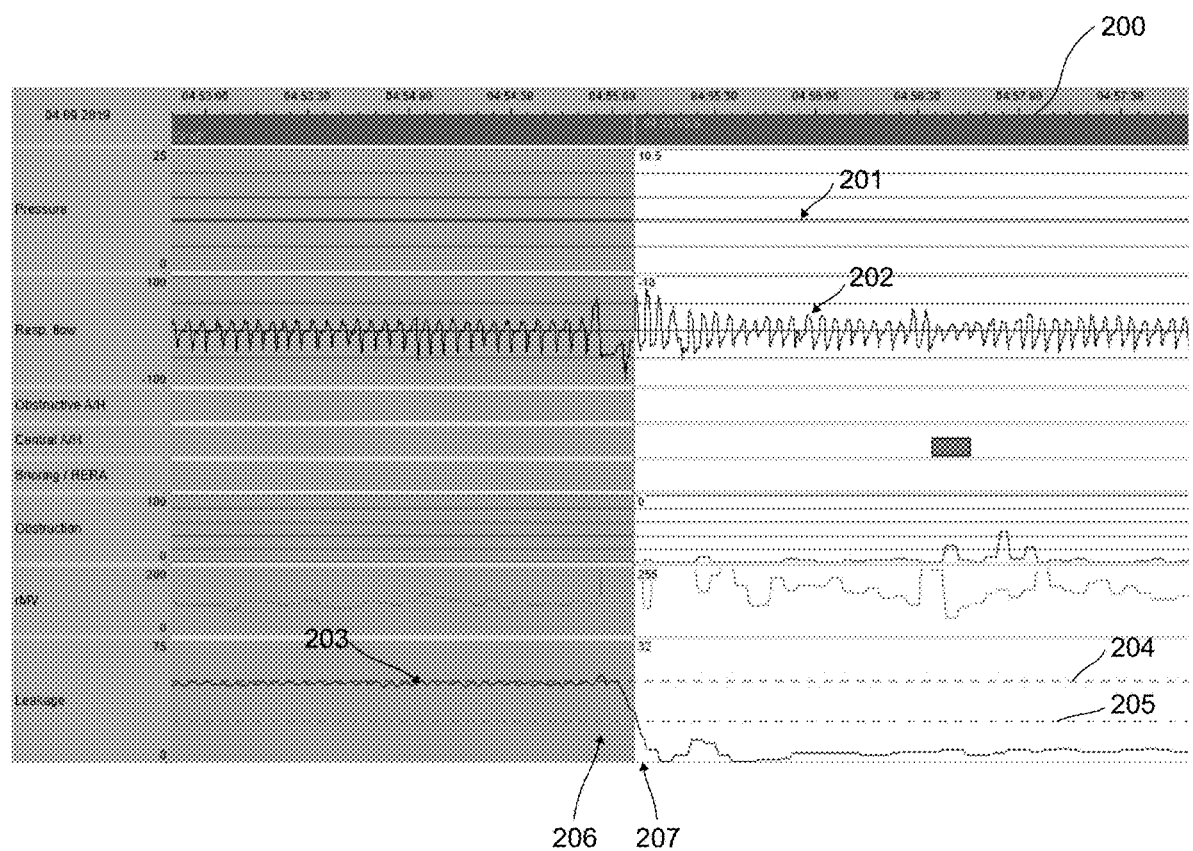
FIGS. 3-4 show further highly schematic graphs with profiles of leakage parameters in order to explain the detection of leakages by means of the invention.

FIG. 3 shows a further example of a respiration profile. Here too, the leakage rate 203 shows a very abrupt leakage reversal 207, which leads to the identification of a mouth leakage 206. The mouth was open for several minutes during ventilation and was then closed, such that the leakage rate 203 has dropped significantly within a few seconds. It can also be clearly seen here that the mouth leakage, in contrast to its end, does not rise abruptly but instead rises slowly over a longer period of time. After closure of the mouth, the leakage rate 203 remains basically zero here, such that there is no mask leakage present here.

Figure 4:
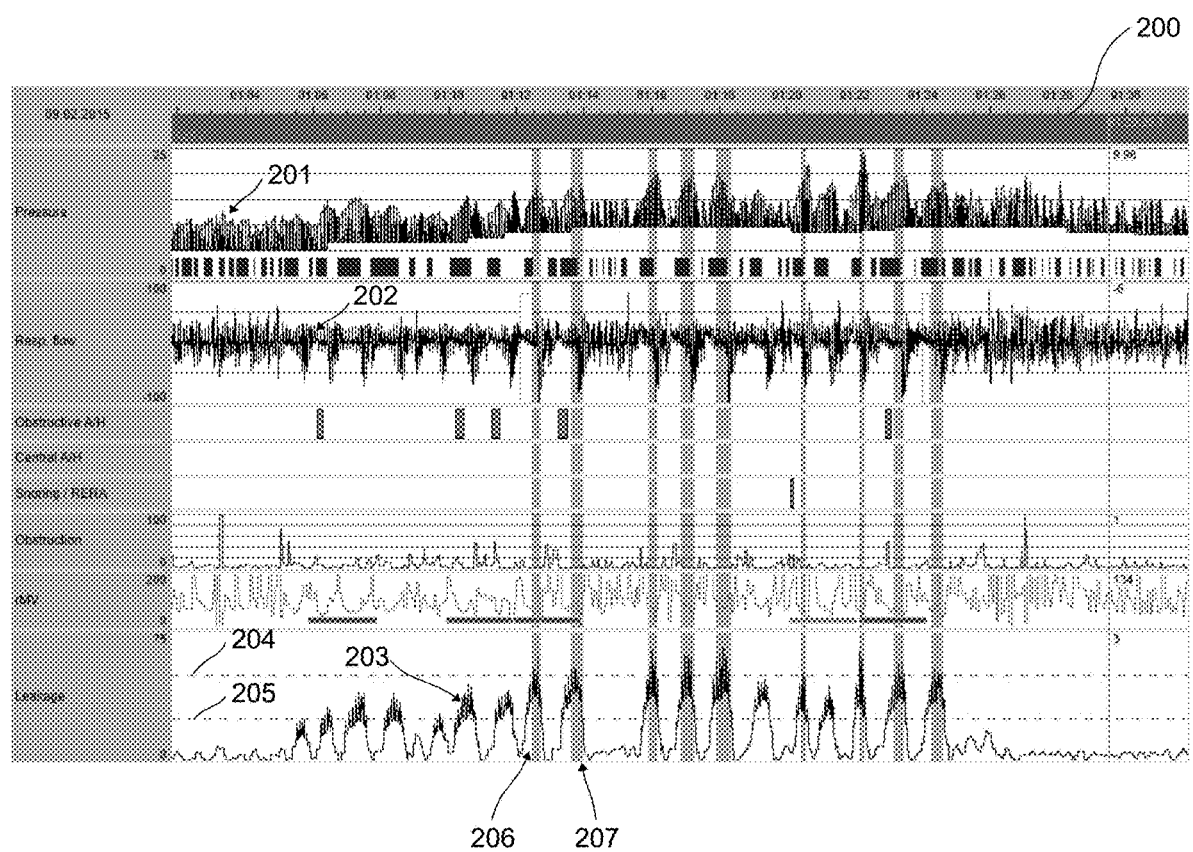

FIG. 4 shows a further example of a respiration profile of a patient with a respiratory disturbance. The patient here opens his mouth periodically and particularly frequently, such that the opening of the mouth corresponds to the breathing pattern. Closure of the mouth takes place in combination with arousal events, which can be detected for example from the characteristic peaks in the flow 202. It will be seen particularly clearly here that abrupt leakage reversals 207 occur upon closure of the mouth. The leakage rate 203 increases here basically only when the mouth is slowly opened again. The regularity of the occurrence of mouth leakages 206 can also be seen particularly clearly here.

To sum up, the present invention provides:
1. A monitoring system for detecting leakages during ventilation with at least one ventilator, wherein the system comprises at least one monitoring device for determining a leakage rate from at least one leakage parameter detected by one or more sensors, the monitoring device being suitable and configured for recording at least one time profile of the leakage parameter, for determining at least one measure for a rate of change of the leakage parameter in a time profile, and for detecting at least one mouth leakage in accordance with the at least one measure, such that a mouth leakage can be differentiated from at least one other leakage type.
2. The monitoring system of item 1, wherein the monitoring device is suitable and configured for detecting the presence of an abrupt leakage reversal using the measure for the rate of change, and for assuming a mouth leakage at least in accordance with an abrupt leakage reversal being present.
3. The monitoring system of one of item 1 or item 2, wherein an abrupt leakage reversal is present when the leakage rate falls by at least about 10% and in particular by at least about 20% within a defined time period.
4. The monitoring system of item 2 or item 3, wherein an abrupt leakage reversal is present when the leakage rate falls by at least a defined measure within a maximum of about 8 breaths and preferably a maximum of about 6 breaths and particularly preferably a maximum of about 4 breaths.
5. The monitoring system of any one of items 2 to 4, wherein the monitoring device is suitable and configured for determining and outputting a characteristic number for the incidence of abrupt leakage reversals per unit of time and in particular per hour.

6. The monitoring system of any one of the preceding items, wherein the monitoring device is suitable and configured for detecting a mouth leakage at least in accordance with whether the at least one leakage parameter changes, in particular decreases, by at least a defined measure within at least one defined time period, such that an abrupt leakage reversal can be assumed.

7. The monitoring system of item 6, wherein the defined time period is a maximum of about 30 seconds and preferably a maximum of about 15 seconds and particularly preferably a maximum of about 10 seconds.

8. The monitoring system of item 6 or item 7, wherein the leakage parameter is a flow of a gas stream relating to the respiration, and wherein a defined measure for the change of the flow is at least a about 10 l/min and preferably at least about 15 l/min and particularly preferably at least about 25 l/min.

9. The monitoring system of any one of the preceding items, wherein the monitoring device is suitable and configured for not taking account and/or for taking only weighted account of a time period in the time profile of the leakage parameter for the detection of the leakage type when the leakage rate, after the abrupt leakage reversal, still lies above a limit value and in particular above about 25 l/min.

10. The monitoring system of any one of the preceding items, wherein the monitoring device is suitable and configured for not outputting the detection of the leakage type and/or for outputting it with at least one warning when the leakage rate, on average and/or over a defined time period, is about 50 l/min or more.

11. The monitoring system of any one of the preceding items, wherein the monitoring device is suitable and configured for detecting the mouth leakage by also at least taking account of how often abrupt leakage reversals occur and/or how regularly abrupt leakage reversals occur.

12. The monitoring system of any one of the preceding items, wherein the monitoring device is suitable and configured for determining a time difference between one abrupt leakage reversal and a past abrupt leakage reversal, and for detecting the mouth leakage by at least also taking account of how great a difference is between successive abrupt leakage reversals.

13. The monitoring system of any one of the preceding items, wherein the monitoring device is suitable and configured for detecting the mouth leakage by also at least taking account of arousal events on the part of the patient, and by considering a time overlap of an arousal event with a start of an abrupt leakage reversal as at least one necessary condition for a presence of a mouth leakage.

14. The monitoring system of any one of the preceding items, wherein the monitoring device is suitable and configured for determining a desired leakage rate by using the leakage rate that still remains after closure of a detected mouth leakage.

15. The monitoring system of any one of the preceding items, wherein the monitoring device is suitable and configured for using a detected mouth leakage as at least one necessary and/or sufficient condition for a detection of an arousal event on the part of the patient.

16. The monitoring system of any one of the preceding items, wherein the monitoring device is suitable and configured for detecting a mask leakage as at least one other leakage type, and for differentiating at least a mouth leakage and a mask leakage from each other.

17. The monitoring system of item 16, wherein the monitoring device is suitable and configured for differentiating the mask leakage from the mouth leakage at least by a duration for which a defined leakage rate is maintained, and/or for differentiating them by a number of defined reversals of the leakage rate, in particular abrupt leakage reversals.

18. The monitoring system of any one of the preceding items, wherein the monitoring device is suitable and configured for carrying out a detection of the leakage type during ventilation at defined time intervals and/or continuously, and for recording detected leakage types and preferably outputting them via at least one display device.

19. The monitoring system of any one of the preceding items, wherein the monitoring device is suitable and configured for executing at least one action in accordance with a detected leakage type, and wherein the action comprises an output of at least one warning and/or alarm and/or an action description for avoiding leakages.

20. The monitoring system of any one of the preceding items, wherein the monitoring device is suitable and configured for actuating the ventilator in accordance with a detected leakage type, and for adapting at least one control variable of the ventilator in order to obtain a decrease in the leakage rate and/or a leakage incidence.

21. The monitoring system of any one of the preceding items, wherein the system further comprises at least one ventilator.

22. A method for operating a monitoring system of any one of the preceding items.

LIST OF REFERENCE NUMERALS 1 monitoring system
2 ventilator
3 monitoring device
4 sensor element
5 display device
6 operating device
12 ventilation device
22 fan
102 breathing mask
103 tubing
200 time
201 pressure
202 flow
203 leakage rate
204 limit value
205 limit value
206 mouth leakage
207 abrupt leakage reversal
208 mask leakage

What is claimed is:

1. A monitoring system for detecting leakages during ventilation with at least one ventilator, wherein the system comprises at least one monitoring device for determining a leakage rate from at least one leakage parameter detected by one or more sensors, the monitoring device being configured for recording at least one time profile of the leakage parameter, for determining at least one measure for a change of the leakage parameter in a time profile, and for detecting a mouth leakage in accordance with the at least one measure, such that the mouth leakage can be differentiated from a mask leakage at least by a duration for which a defined leakage rate is maintained or by a number of defined reversals of the leakage, and wherein the monitoring device is further configured for actuating the ventilator in accordance with a detected leakage type, and for adapting at least one control variable of the ventilator in order to obtain a decrease in the leakage rate and/or a leakage incidence.

2. The monitoring system of claim 1, wherein the monitoring device is configured for detecting a presence of an abrupt leakage reversal using the measure for the rate of change, and for assuming a mouth leakage at least in accordance with an abrupt leakage reversal being present.

3. The monitoring system of claim 1, wherein an abrupt leakage reversal is present when the leakage rate falls by at least 10% within a defined time period.

4. The monitoring system of claim 2, wherein an abrupt leakage reversal is present when the leakage rate falls by at least a defined measure within a maximum of 8 breaths.

5. The monitoring system of claim 2, wherein the monitoring device is configured for determining and outputting a characteristic number for an incidence of abrupt leakage reversals per unit of time.

6. The monitoring system of claim 1, wherein the monitoring device is configured for detecting a mouth leakage at least in accordance with whether the at least one leakage parameter changes by at least a defined measure within at least one defined time period, such that an abrupt leakage reversal can be assumed.

7. The monitoring system of claim 6, wherein the defined time period is a maximum of 30 seconds.

8. The monitoring system of claim 6, wherein the leakage parameter is a flow of a gas stream relating to the respiration, and wherein a defined measure for the change of the flow is at least 10 l/min.

9. The monitoring system of claim 1, wherein the monitoring device is configured for not taking account or for taking only weighted account of a time period in the time profile of the leakage parameter for the detection of the leakage type when the leakage rate, after the abrupt leakage reversal, still lies above a limit value.

10. The monitoring system of claim 1, wherein the monitoring device is configured for not outputting the detection of the leakage type or for outputting it with at least one warning when the leakage rate, on average or over a defined time period, is 50 l/min or more.

11. The monitoring system of claim 1, wherein the monitoring device is configured for detecting the mouth leakage by also at least taking account of how often abrupt leakage reversals occur and/or how regularly abrupt leakage reversals occur.

12. The monitoring system of claim 1, wherein the monitoring device is configured for determining a time difference between one abrupt leakage reversal and a past abrupt leakage reversal, and for detecting the mouth leakage by at least also taking account of how great a difference is between successive abrupt leakage reversals.

13. The monitoring system of claim 1, wherein the monitoring device is configured for detecting the mouth leakage by also at least taking account of arousal events on the part of a patient, and by considering a time overlap of an arousal event with a start of an abrupt leakage reversal as at least one necessary condition for a presence of a mouth leakage.

14. The monitoring system of claim 1, wherein the monitoring device is configured for determining a desired leakage rate by using a leakage rate that still remains after closure of a detected mouth leakage.

15. The monitoring system of claim 1, wherein the monitoring device is configured for using a detected mouth leakage as at least one necessary and/or sufficient condition for a detection of an arousal event on the part of a patient.

16. The monitoring system of claim 1, wherein the monitoring device is configured for carrying out a detection of the leakage type during ventilation at defined time intervals and/or continuously, and for recording detected leakage types.

17. The monitoring system of claim 1, wherein the monitoring device is configured for executing at least one action in accordance with a detected leakage type, and wherein the action comprises an output of at least one warning and/or alarm and/or an action description for avoiding leakages.

18. The monitoring system of claim 1, wherein the leakage parameter is a flow or a pressure of a gas stream relating to the ventilation.

19. A monitoring system for detecting leakages during ventilation with at least one ventilator, wherein the system comprises at least one monitoring device for determining a leakage rate from at least one leakage parameter detected by one or more sensors, the monitoring device being configured for recording at least one time profile of the leakage parameter, for determining at least one measure for a change of the leakage parameter in a time profile, and for detecting a mouth leakage in accordance with the at least one measure, such that the mouth leakage can be differentiated from at least one other leakage type, and further being configured for detecting the mouth leakage by also at least taking account of arousal events on the part of a patient, and by considering a time overlap of an arousal event with a start of an abrupt leakage reversal as at least one necessary condition for a presence of a mouth leakage, and wherein the monitoring device is further configured for actuating the ventilator in accordance with a detected leakage type, and for adapting at least one control variable of the ventilator in order to obtain a decrease in the leakage rate and/or a leakage incidence.

* * * * *